(12) United States Patent
Matsumoto et al.

(10) Patent No.: US 7,847,107 B2
(45) Date of Patent: Dec. 7, 2010

(54) ASYMMETRIC REDUCTION METHOD

(75) Inventors: Yoshinori Matsumoto, Toyama (JP); Yuki Takeuchi, Takaoka (JP); Hiroyuki Yamamoto, Niigata (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 353 days.

(21) Appl. No.: 12/087,092

(22) PCT Filed: Dec. 26, 2006

(86) PCT No.: PCT/JP2006/325875

§ 371 (c)(1),
(2), (4) Date: Aug. 6, 2008

(87) PCT Pub. No.: WO2007/077818

PCT Pub. Date: Jul. 12, 2007

(65) Prior Publication Data

US 2009/0043110 A1   Feb. 12, 2009

(30) Foreign Application Priority Data

Dec. 27, 2005   (JP)   ............... 2005-374989

(51) Int. Cl.
*C07D 209/44*   (2006.01)
(52) U.S. Cl. .................................... 548/470
(58) Field of Classification Search .................. 548/470
See application file for complete search history.

(56) References Cited

FOREIGN PATENT DOCUMENTS

| JP | 5-170718 | 7/1993 |
|----|----------|--------|
| JP | 6-340622 | 12/1994 |
| JP | 2002-507222 | 3/2002 |
| WO | 03/062186 A1 | 7/2003 |

OTHER PUBLICATIONS

K. Aoki et al., "Immobilization of chiral phosphine ligands on silica gel by means of the allylsilane method and their use for catalytic asymmetric reactions", *Tetrahedron: Asymmetry*, vol. 15, No. 11, pp. 1771-1777, (2004).

H. Jendralla et al., "Short and efficient large scale synthesis of (R)-2-benzylsuccinic acid 4-[4-BOC-amino)-1-piperidide] monoamide: N-terminal component of renin inhibitors by asymmetric hydrogenation", *Synlett*, No. 2, pp. 155-157 (Feb. 1993).

*Primary Examiner*—Rei-tsang Shiao
(74) *Attorney, Agent, or Firm*—Peter F. Corless; Christine C. O'Day; Edwards Angell Palmer & Dodge LLP

(57) ABSTRACT

The present invention is to provide a novel method for producing (2S)-2-benzyl-3-(cis-hexahydro-2-isoindolinylcarbonyl)propionic acid which is useful as a therapeutic agent for diabetes. The present invention relates to a method for producing (2S)-2-benzyl-3-(cis-hexahydro-2-isoindolinylcarbonyl)propionic acid, which is characterized in that 2-benzylidene-3-(cis-hexahydro-2-isoindolinylcarbonyl)propionic acid is subjected to a catalytic reduction reaction in the presence of an asymmetric catalyst prepared from a pyrrolidinebisphosphine compound (I) represented by the following general formula (I):

[Chemical formula 4]

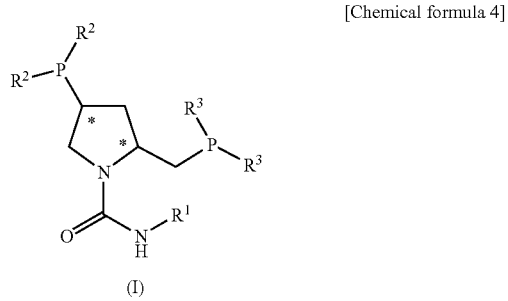

(I)

wherein, $R^1$ represents a linear or branched alkyl group having 1-10 carbon atoms, cycloalkyl group, aralkyl group or aryl group which may respectively have a substituent; and $R^2$ and $R^3$ independently represent an optionally substituted aryl group. The * mark in the pyrrolidine ring shows that the carbon atom at that position has the S configuration, and a rhodium compound.

7 Claims, No Drawings

ASYMMETRIC REDUCTION METHOD

TECHNICAL FIELD

The present invention relates to a novel method for producing (2S)-2-benzyl-3-(cis-hexahydro-2-isoindolinylcarbonyl) propionic acid or a salt thereof, which is useful as a therapeutic agent for diabetes mellitus. More particularly, the present invention relates to a method for producing (2S)-2-benzyl-3-(cis-hexahydro-2-isoindolinylcarbonyl)propionic acid or a salt thereof, by asymmetrically reducing 2-benzylidene-3-(cis-hexahydro-2-isoindolinylcarbonyl)propionic acid.

BACKGROUND ART (2S)-2-Benzyl-3-(cis-hexahydro-2-isoindolinylcarbonyl )propionic acid (hereinafter, may also be referred to as "mitiglinide") or a salt thereof acts as an insulin releasing factor, and thus has a potent blood glucose lowering action (see Patent Document 1). In particular, mitiglinide calcium hydrate [product name: GLUFAST (registered trademark)], which is a preparation utilizing a calcium salt dihydrate of the subject compound, is highly valued as a drug for improving the postprandial blood glucose profile in Type 2 diabetes mellitus.

Although a number of methods for producing mitiglinide and salts thereof have been previously proposed (see Patent Documents 2 and 3), none of these methods provide a reaction yield and optical purity that are necessarily sufficient, and further improvement is needed in order to produce pharmaceutical grade mitiglinide and salts thereof more efficiently. Furthermore, since it is often difficult to purify the very compounds of mitiglinide and salts thereof, it is required to produce mitiglinide with high optical purity during the production steps, at a sufficient conversion rate with a good yield. As a method for producing optically active benzylsuccinic acid, there is known a production method including catalytically reducing benzylidene succinic acid using a chiral diphosphine complex of a transition metal such as ruthenium, as an asymmetric hydrogenation catalyst (see Patent Document 4). However, this method does not offer satisfactory optical purity, and in order to enhance the optical purity, it is necessary to add more purification operations after completion of the catalytic reduction.

Recently, there has been reported a method for producing mitiglinide by subjecting the carbon-carbon double bond moiety of 2-benzylidene-3-(cis-hexahydro-2-isoindolinylcarbonyl)propionic acid (see Patent Document 5), to an asymmetric reduction reaction using a rhodium complex compound having (2S,4S)-N-(t-butoxycarbonyl)-4-diphenylphosphino-2-diphenylphosphinom ethylpyrrolidine (hereinafter, may also be referred to as "BPPM") as an asymmetric ligand (see Patent Document 6). However, the inventors of the present invention performed additional tests on this method, and it was revealed that this method is unsatisfactory as an industrial production method, because the method requires a long time to complete the reaction since the reaction rate is very slow with a conventional amount of the catalyst, and because the molar ratio of the substrate and the asymmetric catalyst (hereinafter, indicated as "S/C") that are required to make the reaction proceed is low, thus it being essential to use expensive noble metal catalysts in large quantities.

As for the asymmetric ligand in the rhodium complex compound for asymmetric reduction, there are also known compounds having dicyclohexylphosphine as the phosphine moiety at the 4-position of pyrrolidine (see Patent Documents 7 and 8), and known are not only carbamate type compounds having a t-butoxycarbonyl group or the like, as in the case of BPPM, as a substituent on the nitrogen atom of pyrrolidine, but also urea type compounds having a t-butylaminocarbonyl group or the like as the substituent (see Patent Documents 7 to 9).

Furthermore, since mitiglinide has a low melting point and is difficult to purify by recrystallization or the like, development of a method capable of producing a benzylsuccinic acid derivative having excellent optical purity, at the highest possible purity that can be provided by the production process, is desired.

Patent Document 1: JP-A No. 4-356459
Patent Document 2: JP-A No. 6-340622
Patent Document 3: JP-A No. 6-340623
Patent Document 4: JP-A No. 5-170718
Patent Document 5: JP-A No. 4-330055
Patent Document 6: JP-T No. 2002-507222
Patent Document 7: Japanese Patent No. 2544926
Patent Document 8: Japanese Patent No. 2617329
Patent Document 9: Japanese patent No. 2816555

DISCLOSURE OF THE INVENTION

Problem to be Solved by the Invention

The present invention is to provide a method for industrially producing mitiglinide with high optical purity.

Means for Solving the Problem

The inventors of the present invention have extensively conducted investigation on industrial production methods for mitiglinide, and as a result, found that when a rhodium complex compound prepared from an asymmetric ligand which is classified as a urea type pyrrolidinebisphosphine compound, such as (2S,4S)-N-phenylaminocarbonyl-4-diphenylphosphino-2-diphenylphosphinomethylpyrrolidine (hereinafter, may also be referred to as "PCPPM"), is used instead of BPPM described as an asymmetric ligand in Patent Document 6, which is classified as a carbamate type pyrrolidinebisphosphine compound, in the reduction of the carbon-carbon double bond moiety of 2-benzylidene-3-(cis-hexahydro-2-isoindolinylcarbonyl)propionic acid, the asymmetric reduction reaction may be performed very efficiently, for a very short time and with a very small amount of catalyst even at a high concentration of substrate, and thus mitiglinide having an industrially high optical purity may be obtained.

That is, the present invention relates to a method for producing (2S)-2-benzyl-3-(cis-hexahydro-2-isoindolinylcarbonyl)propionic acid, characterized in that 2-benzylidene-3-(cis-hexahydro-2-isoindolinylcarbonyl)propionic acid is catalytically reduced in the presence of an asymmetric catalyst prepared from a pyrrolidinebisphosphine compound and a rhodium compound. The present invention also relates to a method for producing a salt and/or a hydrate of the (2S)-2-benzyl-3-(cis-hexahydro-2-isoindolinylcarbonyl)propionic acid produced by the above-described method of the present invention, by reacting the acid with a base substance such as calcium hydroxide.

To be more specific, the present invention includes the following (1) to (10) described below.

(1) A method for producing (2S)-2-benzyl-3-(cis-hexahydro-2-isoindolinylcarbonyl)propionic acid, which comprises catalytically reducing 2-benzylidene-3-(cis-hexahydro-2-isoindolinylcarbonyl) propionic acid in the presence of an asymmetric catalyst prepared from a pyrrolidinebisphosphine compound represented by the following general formula (I):

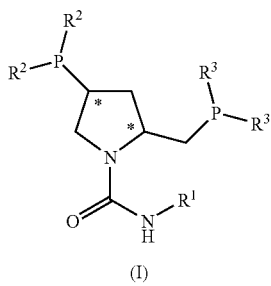

[Chemical Formula 1]

(I)

wherein $R^1$ represents a linear or branched alkyl group having 1 to 10 carbon atoms which may be substituted, a cycloalkyl group which may be substituted, an aralkyl group which may be substituted, or an aryl group which may be substituted; $R^2$ and $R^3$ each independently represent an aryl group which may be substituted; and the mark * in the pyrrolidine ring indicates that the carbon atom at that position has the S configuration, and a rhodium compound.

(2) The method according to (1) above, wherein $R^1$ in the general formula (I) is a linear or branched alkyl group having 1 to 10 carbon atoms which may be substituted, a lower cycloalkyl group having 3 to 7 carbon atoms which may be substituted, a monocyclic, polycyclic or fused ring aryl-alkyl group having 7 to 25 carbon atoms which may be substituted, or a monocyclic, polycyclic or fused ring aryl group having 6 to 20 carbon atoms which may be substituted; and $R^2$ and $R^3$ are each independently a monocyclic, polycyclic or fused ring aryl group having 6 to 20 carbon atoms which may be substituted.

(3) The method according to (1) or (2) above, wherein $R^1$ of the pyrrolidinebisphosphine compound represented by the general formula (I) is a linear or branched alkyl group having 1 to 10 carbon atoms, a phenylalkyl group which may have an alkenyl group as a substituent, or a phenyl group which may have a halogen atom as a substituent.

(4) The method according to any one of (1) to (3) above, wherein $R^2$ and $R^3$ of the pyrrolidinebisphosphine compound represented by the general formula (I) are each independently a phenyl group which may have an alkyl group or alkoxy group having 1 to 10 carbon atoms as a substituent.

(5) The method according to any one of (1) to (4) above, wherein the substituents of the alkyl group, cycloalkyl group, aralkyl group or aryl group for $R^1$, $R^2$ and $R^3$ of the pyrrolidinebisphosphine compound represented by the general formula (I), include one or two or more groups selected from the group consisting of a linear or branched lower alkyl group having 1 to 10 carbon atoms, a lower alkenyl group having 2 to 10 carbon atoms, a linear or branched lower alkoxy group having 1 to 10 carbon atoms, a halogen atom, and a lower alkoxycarbonyl group in which a linear or branched lower alkoxy group having 1 to 10 carbon atoms is bound to a carbonyl group.

(6) The method according to (5) above, wherein the substituents of the alkyl group in the general formula (I) include one or two or more selected from a halogen atom, an alkoxy group and an alkoxycarbonyl group.

(7) The method according to any one of (1) to (6) above, wherein the pyrrolidinebisphosphine compound represented by the general formula (I) is selected from the group consisting of
(2S,4S)-N-phenylaminocarbonyl-4-diphenylphosphino-2-diphenylphosphinomethylpyrrolidine,
(2S,4S)-N-3,4-dichlorophenylaminocarbonyl-4-diphenylphosphino-2-diphenylphosphinomethylpyrrolidine,
(2S,4S)-N-t-butylaminocarbonyl-4-diphenylphosphino-2-diphenylphosphinomethylpyrrolidine,
(2S,4S)-N-methylaminocarbonyl-4-diphenylphosphino-2-diphenylphosphinomethylpyrrolidine,
(2S,4S)-N-1S-phenylethylaminocarbonyl-4-diphenylphosphino-2-diphenylphosphinomethylpyrrolidine,
(2S,4S)-N-1R-phenylethylaminocarbonyl-4-diphenylphosphino-2-diphenylphosphinomethylpyrrolidine, and
(2S,4S)-N-1-(3-isopropenylphenyl)-1-methylethylaminocarbonyl-4-diphenylphosphino-2-diphenylphosphinomethylpyrrolidine.

(8) The method according to any one of (1) to (7) above, wherein the rhodium compound is a rhodium complex having ethylene, 1,5-cyclooctadiene or 2,5-norbornadiene as a ligand.

(9) A method for producing a salt of (2S)-2-benzyl-3-(cis-hexahydro-2-isoindolinylcarbonyl)propionic acid, which includes reacting the (2S)-2-benzyl-3-(cis-hexahydro-2-isoindolinylcarbonyl)propionic acid produced by the method according to any one of (1) to (8) above, with a basic substance.

(10) The method according to (9) above, wherein the salt of (2S)-2-benzyl-3-(cis-hexahydro-2-isoindolinylcarbonyl)propionic acid is a calcium salt.

In the present specification, the term alkyl group means a linear or branched lower alkyl group having 1 to 10 carbon atoms, and preferably 4 to 10 carbon atoms. Specific examples of the alkyl group according to the present invention include, for example, a methyl group, an ethyl group, an n-propyl group, an isopropyl group, an n-butyl group, an s-butyl group, a t-butyl group, an n-pentyl group, an isopentyl group, an s-pentyl group, a t-pentyl group, a neopentyl group, a hexyl group, a heptyl group, an octyl group, a nonyl group, a decyl group and the like.

In the present specification, the term cycloalkyl group means a lower cycloalkyl group having 3 to 7 carbon atoms, and preferably 5 to 7 carbon atoms. Specific examples of the cycloalkyl group according to the present invention include, for example, a cyclopropyl group, a cyclobutyl group, a cyclopentyl group, a cyclohexyl group, a cycloheptyl group, and the like.

In the present specification, the term aryl group means a monocyclic, polycyclic or fused ring aryl group having 6 to 20 carbon atoms, and preferably 6 to 12 carbon atoms. More specifically, amonocyclic, polycyclic or fused ring carbocyclic aromatic group having 6 to 20 carbon atoms, and preferably 6 to 12 carbon atoms, may be mentioned. Specific examples of aryl according to the present invention include, for example, a phenyl group, a naphthyl group and the like.

In the present specification, the term aralkyl group means a monocyclic, polycyclic or fused ring aryl-alkyl group having 7 to 25 carbon atoms, and preferably 7 to 13 carbon atoms. The aralkyl group according to the present invention is preferably a phenylalkyl group, and specific examples of the phenylalkyl group include, for example, a benzyl group, a 1-phenylethyl group, a 2-phenylethyl group, an α,α-dimethylbenzyl group, and the like.

In the present specification, the term alkoxy group means a lower alkoxy group in which an oxygen atom is bound to a linear or branched alkyl group having 1 to 10 carbon atoms, and preferably 1 to 7 carbon atoms. Specific examples of the alkoxy group according to the present invention include, for example, a methoxy group, an ethoxy group, an n-propyloxy group, an isopropyloxy group, and the like.

In the present specification, the term halogen atom means an atom selected from the group consisting of a fluorine atom, a chlorine atom, a bromine atom and an iodine atom. Preferred halogen atoms according to the present invention include, for example, a chlorine atom, a bromine atom, and the like.

In the present specification, the term alkenyl group means a lower alkenyl group having 2 to 10 carbon atoms, and preferably 2 to 6 carbon atoms. Specific examples of the alkenyl group according to the present invention include, for example, a vinyl group, an n-propenyl group, an isopropenyl group, and the like.

In the present specification, the term alkoxycarbonyl group means a lower alkoxycarbonyl group in which an oxycarbonyl group is bound to a linear or branched lower alkyl group having 1 to 10 carbon atoms, and preferably 1 to 7 carbon atoms. Specific examples of the alkoxycarbonyl group according to the present invention include a methoxycarbonyl group, an ethoxycarbonyl group, a t-butoxycarbonyl group, and the like.

The urea type pyrrolidinebisphosphine compound used in the present invention is (2S,4S)-N-substituted aminocarbonyl-4-diarylphosphino-2-diarylphosphinomethylpyrrolidine represented by the following general formula (I):

[Chemical Formula 2]

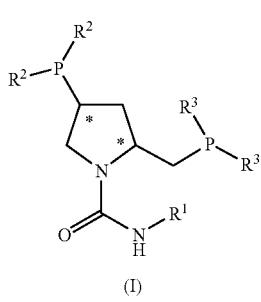

(I)

wherein $R^1$ represents a linear or branched alkyl group having 1 to 10 carbon atoms which may be substituted, a cycloalkyl group which may be substituted, an aralkyl group which may be substituted, or an aryl group which may be substituted; $R^2$ and $R^3$ each independently represent an aryl group which may be substituted; and the mark * in the pyrrolidine ring indicates that the carbon atom at that position has the S configuration.

The alkyl group, cycloalkyl group, aralkyl group and aryl group in the general formula (I) may be substituted with substituents, if necessary, and examples of such substituents include one or two or more selected from the group consisting of the above-described alkyl group, alkenyl group, alkoxy group, halogen atom and alkoxycarbonyl group. More specifically, examples of the substituent which the alkyl group may have include a halogen atom, an alkoxy group, an alkoxycarbonyl group and the like.

Examples of the substituents which the cycloalkyl group, aryl group or aralkyl group may have include a halogen atom, an alkyl group, an alkenyl group, an alkoxy group, an alkoxycarbonyl group and the like.

Preferred examples of $R^1$ for the general formula (I) include a lower alkyl group, a phenylalkyl group which may have an alkenyl group as a substituent, a phenyl group which may have a halogen atom as a substituent, and the like. The phenylalkyl group which have an alkenyl group as a substituent may be exemplified by a 1-(3-isopropenylphenyl)-1-methylethyl group, or the like. The phenyl group which have a halogen atom as a substituent may be exemplified by a 3,4-dichlorophenyl group, or the like.

Preferred examples of $R^2$ or $R^3$ for the general formula (I) include a phenyl group which may have an alkyl group or alkoxy group as a substituent, and a more preferred group may be a phenyl group.

Preferred examples of the urea type pyrrolidinebisphosphine compound include:

(2S,4S)-N-phenylaminocarbonyl-4-diphenylphosphino-2-diphenylphosphinomethylpyrrolidine (PCPPM), (2S,4S)-N-3,4-dichlorophenylaminocarbonyl-4-diphenylphosphino-2-diphenylphosphinomethylpyrrolidine (hereinafter, referred to "DCPCPPM"), (2S,4S)-N-t-butylaminocarbonyl-4-diphenylphosphino-2-diphenylphosphinomethylpyrrolidine (hereinafter, referred to as "BCPPM"), (2S,4S)-N-methylaminocarbonyl-4-diphenylphosphino-2-diphenylphosphinomethylpyrrolidine (hereinafter, referred to as "MCPPM"), (2S,4S)-N-(1S)-1-phenylethylaminocarbonyl-4-diphenylphosphino-2-diphenylphosphinomethylpyrrolidine (hereinafter, referred to as "SSS-C*PPM"), (2S,4S)-N-(1R)-1-phenylethylaminocarbonyl-4-diphenylphosphino-2-diphenylphosphinomethylpyrrolidine (hereinafter, referred to as "SSR-C*PPM"), (2S,4S)-N-1-(3-isopropenylphenyl)-1-methylethylaminocarbonyl-4-diphenylphosphino-2-diphenylphosphinomethylpyrrolidine (hereinafter, referred to as "DMPCPPM"), and the like.

2-Benzylidene-3-(cis-hexahydro-2-isoindolinylcarbonyl) propionic acid, which is a raw material compound in the method of the present invention, can be produced by the methods described in Patent Document 6, but the method is not limited to those.

The asymmetric catalyst used in the method of the present invention is prepared from an optically active pyrrolidinebisphosphine compound represented by the general formula (I) shown above, and a rhodium compound, preferably a rhodium complex, and the asymmetric catalyst is preferably a rhodium complex compound having the optically active pyrrolidinebisphosphine compound represented by the general formula (I) as a ligand. Such rhodium complex compound can be easily prepared according to a method described in any of Patent Documents 8 and 9, for example, from the urea type pyrrolidinebisphosphine compound represented by the general formula (I) and a rhodium compound, preferably a monovalent rhodium complex.

The rhodium compound, preferably rhodium complex, used in the preparation of the catalyst of the present invention is not particularly limited, but the rhodium complex is preferably, for example, a rhodium complex having ethylene, 1,5-cyclooctadiene or 2,5-norbornadiene as a ligand. Examples of such rhodium complex include a bis (ethylene) rhodium-chloride complex, an (acetylacetonato)(η-1,5-cyclooctadiene)rhodium complex, an (acetylacetonato)dicarbonyl rhodium complex, a rhodium-1,5-cyclooctadiene-chloride complex, a rhodium-1,5-cyclooctadiene-tetrafluoroboric acid complex, a rhodium-2,5-norbornadiene-chloride complex, a rhodium-2,5-norbornadiene-tetrafluoroboric acid complex, a rhodium-1,5-cyclooctadiene-trifluoromethanesulfonic acid complex, a rhodium-1,5-cyclooctadiene-hexafluorophosphoric acid complex, and the like. Furthermore, the rhodium complex may also be supported on an insoluble solid surface of silica gel, alumina or the like, and for example, a CATAXA/rhodium-1,5-cyclooctadiene complex or the like may be mentioned.

The asymmetric catalyst can be prepared by mixing a pyrrolidinebisphosphine compound and a rhodium compound, preferably a rhodium complex, in a solvent. The catalyst may also be prepared directly in the reaction system, by mixing the compounds in the reaction solvent.

The ratio of the pyrrolidinebisphosphine compound to the rhodium compound is 0.5 to 10 moles relative to 1 mole of rhodium atoms, and preferably 1 to 5 moles relative to 1 mole of rhodium atoms.

As for the amount of rhodium metal in the asymmetric reaction, the rhodium metal is used in an amount of 1/2000 to 1/100000 moles, preferably 1/5000 to 1/30000 moles, and more preferably 1/10000 to 1/20000 moles, relative to 1 mole of the raw material 2-benzylidene-3-(cis-hexahydro-2-isoindolinylcarbonyl)propionic acid. As this amount is expressed as the molar ratio of substrate and asymmetric catalyst (S/C), S/C is 2000 to 100000, preferably 5000 to 30000, and more preferably 10000 to 20000.

The method of the present invention can also be performed with an immobilized catalyst. By using an immobilized catalyst, separation of the catalyst becomes easy, and further, the catalyst can be used repeatedly in the asymmetric reduction reaction. The asymmetric catalyst used in the immobilized catalyst is preferably in the form of an immobilized layer supported on a support such as silica gel or alumina. A preferred rhodium complex for the preparation of such catalyst may be exemplified by a CATAXA/rhodium-1,5-cyclooctadiene complex, or the like. Furthermore, the molar ratio of substrate and asymmetric catalyst (S/C) in the immobilized catalyst is preferably set to about ½ to ¹⁄₁₀ of the value in the case of a homogeneous catalyst system, for example, about 200 to 10000, and preferably 500 to 5000, but the value is not to be limited to this range.

Examples of the solvent used in the asymmetric reduction reaction according to the present invention include alcohols such as methanol, ethanol and isopropyl alcohol; solvent mixtures of alcohols and organic solvents such as toluene, tetrahydrofuran, acetone, methyl isobutyl ketone and chloroform; solvent mixtures of water and alcohols; and the like.

The hydrogen pressure in the asymmetric reduction reaction is typically 0.1 to 15 MPa, and is preferably 0.1 to 2 MPa, and particularly preferably 0.2 to 1 MPa. The reaction temperature may be approximately 0 to 150° C., preferably 10 to 100° C., and particularly preferably 10 to 50° C.

The asymmetric catalyst of the present invention prepared from the pyrrolidinebisphosphine compound represented by the above general formula (I) and a rhodium compound, has a very strong catalytic activity against the raw material compound of the present invention, 2-benzylidene-3-(cis-hexahydro-2-isoindolinylcarbonyl)propionic acid. Furthermore, as will be described in the following Examples, the asymmetric catalyst of the invention allows the reaction to proceed sufficiently even at an S/C ratio of 10000 or greater, and can achieve a conversion rate of 97% or higher, and typically a conversion rate of approximately 100%, within an extremely short reaction time of, for example, about 4 hours. This is believed to be because the asymmetric catalyst of the present invention has very excellent substrate specificity toward the raw material compound of the present invention, 2-benzylidene-3-(cis-hexahydro-2-isoindolinylcarbonyl)propionic acid. Therefore, since the asymmetric reduction reaction of 2-benzylidene-3-(cis-hexahydro-2-isoindolinylcarbonyl) propionic acid involving the asymmetric catalyst of the present invention can be completed in an extremely short time compared with conventional asymmetric reduction reactions, the reaction time for the method of the present invention is often sufficient with 0.5 to 100 hours or 0.5 to 10 hours, preferably 2 to 20 hours, and more preferably 2 to 10 hours.

According to the method of the present invention, a conversion rate of nearly 100% can be achieved in an extremely short reaction time, and thus the desired material can be produced with high purity and with a high yield.

The method of the present invention for producing a salt of (2S)-2-benzyl-3-(cis-hexahydro-2-isoindolinylcarbonyl) propionic acid can be performed by a conventional salification reaction. That is, the reaction can be performed by adding a basic substance such as calcium hydroxide to the acid in free form produced by the asymmetric reduction reaction which has been described in the above, and mixing the mixture under stirring. As for the solvent, water, aqueous alcohol or the like can be used.

This method can be performed after isolating the acid in free form produced by the asymmetric reduction reaction that has been described in the above. However, as described above, since a desired substance with high purity can be produced in the method involving the asymmetric reduction reaction of the present invention, the method can also be performed without isolating by diluting the reaction mixture obtained after completion of the asymmetric reduction reaction, if necessary, with water or alcohol, and then directly adding a basic substance to the reaction mixture.

The salt produced by the method of the present invention may be a hydrate containing water of crystallization.

EFFECT OF THE INVENTION

According to the asymmetric reduction method of the present invention, mitiglinide with high optical purity can be produced from 2-benzylidene-3-(cis-hexahydro-2-isoindolinylcarbonyl) propionic acid, with a small amount of catalyst in a short time.

The present invention is illustrated in more detail by the following examples, but should not be construed to be limited thereto.

In addition, 2-benzylidene-3-(cis-hexahydro-2-isoindolinylcarbonyl) propionic acid was produced according to the method described in Patent Document 6.

EXAMPLE 1

(1) Preparation Example with S/C Ratio of 10000

2-Benzylidene-3-(cis-hexahydro-2-isoindolinylcarbonyl) propionic acid (15 g) and 59 mL of methanol were introduced into an autoclave, and a catalyst prepared from 3.02 mg of PCPPM, 1.18 mg of rhodium-1,5-cyclooctadiene-chloride complex and 1 mL of methanol was added thereto (S/C=10000). The mixture was allowed to react at room temperature and at a hydrogen pressure of 0.5 MPa for 4 hours.

2-Benzylidene-3-(cis-hexahydro-2-isoindolinylcarbonyl) propionic acid was not detected by high performance liquid chromatography, and the optical purity of mitiglinide thus obtained was 95.1% e.e.

(2) Preparation Example with S/C Ratio of 20000

The method of (1) was performed with an S/C ratio of 20000 for a reaction time of 16 hours. As a result, the residual ratio of the raw material obtained by high performance liquid chromatography was 1.27%, and the optical purity was 95.2% e.e.

EXAMPLE 2

(1) Preparation Example with S/C Ratio of 10000

The preparation was carried out in the same manner as in Example 1, except that 3.38 mg of DCPCPPM (S/C=10000) was used instead of 3.02 mg of PCPPM of Example 1. After the reaction, the residual ratio of 2-benzylidene-3-(cis-hexahydro-2-isoindolinylcarbonyl)propionic acid obtained by high performance liquid chromatography was 0.44%, and the optical purity of mitiglinide thus obtained was 94.6% e.e.

(2) Preparation Example with S/C Ratio of 20000

The method of (1) was performed with an S/C ratio of 20000 for a reaction time of 16 hours. As a result, it was not possible to detect the raw material by high performance liquid chromatography. The optical purity of the product was 94.4% e.e.

EXAMPLE 3

The preparation was carried out in the same manner as in Example 1, except that 2.91 mg of BCPPM was used instead of 3.02 mg of PCPPM of Example 1. After the reaction, 2-benzylidene-3-(cis-hexahydro-2-isoindolinylcarbonyl)propionic acid was not detected, and the optical purity of mitiglinide thus obtained was 96.6% e.e.

EXAMPLE 4

The preparation was carried out in the same manner as in Example 1, except that 3.16 mg of SSR-C*PPM was used instead of 3.02 mg of PCPPM of Example 1. After the reaction, the residual ratio of 2-benzylidene-3-(cis-hexahydro-2-isoindolinylcarbonyl)propionic acid was 0.55%, and the optical purity of mitiglinide thus obtained was 96.3% e.e.

EXAMPLE 5

(1) Preparation Example with S/C Ratio of 10000

The preparation was carried out in the same manner as in Example 1, except that 3.44 mg of DMPCPPM (S/C=10000) was used instead of 3.02 mg of PCPPM of Example 1. After the reaction, the residual ratio of 2-benzylidene-3-(cis-hexahydro-2-isoindolinylcarbonyl)propionic acid obtained by high performance liquid chromatography was 0.02%, and the optical purity of mitiglinide thus obtained was 96.4% e.e.

Preparation Example with S/C Ratio of 20000

The method of (1) was performed with an S/C ratio of 20000 for a reaction time of 16 hours. As a result, it was not possible to detect the raw material by high performance liquid chromatography. The optical purity of the product was 96.4% e.e.

EXAMPLE 6

The preparation was carried out in the same manner as in Example 1, except that 1.10 mg of rhodium-2,5-norbornadienechloride complex (S/C=10000) was used instead of 1.18 mg of rhodium-1,5-cyclooctadiene-chloride complex of Example 1. After the reaction, 2-benzylidene-3-(cis-hexahydro-2-isoindolinylcarbonyl)propionic acid was not detected, and the optical purity of mitiglinide thus obtained was 95.5% e.e.

EXAMPLE 7

The preparation was carried out in the same manner as in Example 1, except that 1.79 mg of rhodium-2,5-norbornadienetetrafluoroboric acid complex (S/C=10000) was used instead of 1.18 mg of rhodium-1,5-cyclooctadiene-chloride complex of Example 1. After the reaction, the residual ratio of 2-benzylidene-3-(cis-hexahydro-2-isoindolinylcarbonyl)propionic acid was 0.12%, and the optical purity of mitiglinide thus obtained was 96.0% e.e.

EXAMPLE 8

The preparation was carried out in the same manner as in Example 1, except that 2.24 mg of rhodium-1,5-cyclooctadienetrifluoromethanesulfonic acid complex (S/C=10000) was used instead of 1.18 mg of rhodium-1,5-cyclooctadiene-chloride complex of Example 1. After the reaction, 2-benzylidene-3-(cis-hexahydro-2-isoindolinylcarbonyl)propionic acid was not detected, and the optical purity of mitiglinide thus obtained was 95.9% e.e.

EXAMPLE 9

The preparation was carried out in the same manner as in Example 1, except that 1.94 mg of rhodium-1,5-cyclooctadiene-tetrafluoroboric acid complex hydrate (S/C=10000) was used instead of 1.18 mg of rhodium-1,5-cyclooctadiene-chloride complex of Example 1. After the reaction, the residual ratio of 2-benzylidene-3-(cis-hexahydro-2-isoindolinylcarbonyl)propionic acid was 2.21%, and the optical purity of mitiglinide thus obtained was 95.9% e.e.

EXAMPLE 10

The preparation was carried out in the same manner as in Example 1, except that 10.04 mg of PCPPM was used instead of 3.02 mg of PCPPM of Example 1, and 328 mg of CAT-AXA/rhodium-1,5-cyclooctadiene complex (S/C=3,000), which is an immobilized rhodium, was used instead of 1.18 mg of rhodium-1,5-cyclooctadiene-chloride complex of Example 1. After the reaction, 2-benzylidene-3-(cis-hexahydro-2-isoindolinylcarbonyl)propionic acid was not detected, and the optical purity of mitiglinide thus obtained was 95.5% e.e.

COMPARATIVE EXAMPLE 1

The preparation was carried out in the same manner as in Example 1, except that 3.02 mg of (2S,4S)-N-phenyloxycarbonyl-4-diphenylphosphino-2-diphenylphosphinomethylpyrrolidine (PPPM) was used instead of 3.02 mg of PCPPM of Example 1. After the reaction, the residual ratio of 2-benzylidene-3-(cis-hexahydro-2-isoindolinylcarbonyl)propionic acid was 9.74%, and the optical purity of mitiglinide thus obtained was 94.5% e.e.

COMPARATIVE EXAMPLE 2

The preparation was carried out in the same manner as in Example 1, except that 2.92 mg of BPPM was used instead of 3.02 mg of PCPPM of Example 1. After the reaction, the residual ratio of 2-benzylidene-3-(cis-hexahydro-2-isoindolinylcarbonyl)propionic acid was 10.85%, and the optical purity of mitiglinide thus obtained was 96.1% e.e.

As discussed in the above, the urea type pyrrolidinebis phosphine compounds as asymmetric ligands are more excellent in all of the optical purity, reaction rate and S/C ratio, compared with the carbamate type pyrrolidinebisphosphine compounds. Therefore, the production method according to the present invention is an industrially excellent production method capable of providing high optical purity, shortening the reaction time, and reducing the amount of catalyst.

EXAMPLE 11

2-Benzylidene-3-(cis-hexahydro-2-isoindolinylcarbonyl) propionic acid (15 g) and 59 mL of methanol were introduced into an autoclave, and a catalyst prepared from 7.5 mg of PCPPM and 2.9 mg of rhodium-1,5-cyclooctadiene-chloride complex was added thereto. The mixture was allowed to react at room temperature and at a hydrogen pressure of 0.5 MPa. After 4 hours, the reaction solution was removed from the autoclave, and 60 mL of methanol and 1.7 g of calcium hydroxide were added thereto. The mixture was stirred for 30 minutes, and then 120 mL of water was added to the mixture. After stirring for 2 hours, crystals were filtered, washed with water, and then dried, to obtain mitiglinide calcium salt dihydrate.

INDUSTRIAL APPLICABILITY

The method of the present invention is to provide a novel method for producing (2S)-2-benzyl-3-(cis-hexahydro-2-isoindolinylcarbonyl)propionic acid represented by the general formula (I) or a salt thereof, which is useful as a therapeutic agent for diabetes mellitus, efficiently and with high purity. Thus, the method is highly useful in the pharmaceutical field, and has industrial applicability.

The invention claimed is:

1. A method for producing (2S)-2-benzyl-3-(cis-hexahydro-2-isoindolinylcarbonyl)propionic acid, which comprises catalytically reducing 2-benzylidene-3-(cis-hexahydro-2-isoindolinylcarbonyl)propionic acid in the presence of an asymmetric catalyst prepared from a pyrrolidinebisphosphine compound represented by the following general formula (I):

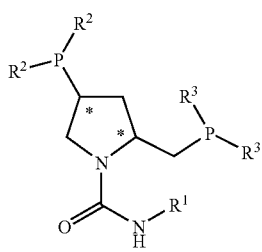

(I)

wherein $R^1$ represents a linear or branched alkyl group having 1 to 10 carbon atoms which may be substituted, a cycloalkyl group which may be substituted, an aralkyl group which may be substituted, or an aryl group which may be substituted; $R^2$ and $R^3$ each independently represent an aryl group which may be substituted; and the mark * in the pyrrolidine ring indicates that the carbon atom at that position has the S configuration, and a rhodium compound.

2. The method according to claim 1, wherein $R^1$ of the pyrrolidinebisphosphine compound represented by the general formula (I) is a linear or branched alkyl group having 1 to 10 carbon atoms, a phenylalkyl group which may have an alkenyl group as a substituent, or a phenyl group which may have a halogen atom as a substituent.

3. The method according to claim 1, wherein $R^2$ and $R^3$ of the pyrrolidinebisphosphine compound represented by the general formula (I) are each independently a phenyl group which may have an alkyl group or alkoxy group having 1 to 10 carbon atoms as a substituent.

4. The method according to claim 1, wherein the pyrrolidinebisphosphine compound represented by the general formula (I) is selected from the group consisting of (2S,4S)-N-phenylaminocarbonyl-4-diphenylphosphino-2-diphenylhosphinomethylpyrrolidine, (2S,4S)-N-3,4-dichlorophenylaminocarbonyl-4-diphenylphosphino-2-diphenylphosphinomethylpyrrolidine, (2S,4S)-N-t-butylaminocarbonyl-4-diphenylphosphino-2-diphenylphosphinomethylpyrrolidine, (2S,4S)-N-methylaminocarbonyl-4-diphenylphosphino-2-diphenylphosphinomethylpyrrolidine, (2S,4S)-N-1S-phenylethylaminocarbonyl-4-diphenylphosphino-2-diphenylphosphinomethylpyrrolidine, (2S,4S)-N-1R-phenylethylaminocarbonyl-4-diphenylphosphino-2-diphenylphosphinomethylpyrrolidine, and (2S,4S)-N-1-(3-isopropenylphenyl)-1-methylethylaminocarbonyl-4-diphenylphosphino-2-diphenylphosphinomethylpyrrolidine.

5. The method according to claim 1, wherein the rhodium compound is a rhodium complex having ethylene, 1,5-cyclooctadiene or 2,5-norbornadiene as a ligand.

6. A method for producing a salt of (2S)-2-benzyl-3-(cis-hexahydro-2-isoindolinylcarbonyl)propionic acid, which comprises reacting (2S)-2-benzyl-3-(cis-hexahydro-2-isoindolinylcarbonyl)propionic acid produced by the method according to claim 1, with a basic substance.

7. The method according to claim 6, wherein the salt of (2S)-2-benzyl-3-(cis-hexahydro-2-isoindolinylcarbonyl) propionic acid is a calcium salt.

* * * * *